(12) United States Patent
Qin et al.

(10) Patent No.: US 10,450,512 B2
(45) Date of Patent: Oct. 22, 2019

(54) SINGLE-LOOP OCTANE ENRICHMENT

(71) Applicant: PRIMUS GREEN ENERGY INC., Hillsborough, NJ (US)

(72) Inventors: Meifang Qin, Princeton, NJ (US); Howard L. Fang, Bridgewater, NJ (US); Zhong He, Harrison, NJ (US); Ricardo Orench, Langhorne, PA (US); Zhiyi Wu, Hillsborough, NJ (US); Arie Toren, Kendall Park, NJ (US)

(73) Assignee: Primus Green Energy Inc., Hillsborough, NJ (US)

( * ) Notice: Subject to any disclaimer, the term of this patent is extended or adjusted under 35 U.S.C. 154(b) by 1 day.

(21) Appl. No.: 15/428,956

(22) Filed: Feb. 9, 2017

(65) Prior Publication Data

US 2017/0226427 A1    Aug. 10, 2017

Related U.S. Application Data

(60) Provisional application No. 62/293,410, filed on Feb. 10, 2016.

(51) Int. Cl.
| | |
|---|---|
| *C10G 3/00* | (2006.01) |
| *C10G 35/095* | (2006.01) |
| *C10L 1/06* | (2006.01) |
| *C07C 29/152* | (2006.01) |
| *C07C 41/09* | (2006.01) |

(52) U.S. Cl.
CPC ............. *C10G 3/49* (2013.01); *C07C 29/152* (2013.01); *C07C 41/09* (2013.01); *C10G 35/095* (2013.01); *C10L 1/06* (2013.01); *C10G 2400/02* (2013.01); *C10G 2400/30* (2013.01); *C10L 2270/023* (2013.01)

(58) Field of Classification Search
CPC ..... C07C 29/152; C07C 41/09; C07C 29/151; C07C 31/04; C07C 43/043; C07C 1/041; C10L 1/06; C10L 2270/023; B01J 2219/0004; B01J 8/0449; C10G 2400/02; C10G 2400/30; C10G 35/095; C10G 3/49; C10G 2300/1022; C10G 2300/304; C10G 2300/4025; C10G 2300/4081; C10G 2400/04; C10G 2400/08; C10G 2/32; C10G 2/33; C10G 2/331; C10G 2/332; C10G 3/42; C10G 3/46; C10G 3/48; C10G 45/58; C10G 45/60
See application file for complete search history.

(56) References Cited

U.S. PATENT DOCUMENTS

| | | | |
|---|---|---|---|
| 4,304,951 A | 12/1981 | Garwood et al. | |
| 4,347,397 A | 8/1982 | Dwyer et al. | |
| 4,387,261 A | 6/1983 | Chester et al. | |
| 4,973,784 A | 11/1990 | Han et al. | |
| 7,462,275 B2 * | 12/2008 | Das | C10G 11/05 208/113 |
| 8,569,554 B1 | 10/2013 | Fang et al. | |
| 8,686,206 B2 * | 4/2014 | Fang | B01J 8/0449 585/14 |
| 8,722,951 B2 | 5/2014 | Fang et al. | |
| 9,169,166 B2 | 10/2015 | Fang et al. | |
| 9,670,416 B2 * | 6/2017 | Fang | C07C 29/1516 |
| 2016/0168476 A1 | 6/2016 | Fang et al. | |

* cited by examiner

*Primary Examiner* — Sharon Pregler
(74) *Attorney, Agent, or Firm* — Berenato & White, LLC

(57) ABSTRACT

The present invention provides apparatuses and processes for producing high octane fuel from synthesis gas. The process combines transalkylation and zeolite-forming/aromatization in conjunction with a single recycle loop configuration in order to effectively promote the fuel quality, particularly octane rating. The process involves adding a step for enriching octane of the fuel coming from the single recycle loop process. Preferably, the enrichment step takes place in an octane enrichment reactor containing two different catalysts, a zeolite-forming/aromatization catalyst followed by a transalkylation catalyst. The final fuel product preferably has an octane of about 92 to about 112.

12 Claims, 7 Drawing Sheets

SINGLE-LOOP OCTANE ENRICHMENT

CROSS-REFERENCE TO RELATED APPLICATIONS AND CLAIM TO PRIORITY

This application claims priority to U.S. Provisional Patent Application No. 62/293,410, filed Feb. 10, 2016, which is incorporated herein by reference.

FIELD OF THE INVENTION

The present invention relates to apparatuses and processes for producing high octane fuel, particularly from US medium octane gas produced from synthesis gas.

BACKGROUND

When hydrocarbon stream passes through an acidic zeolite catalyst, two typical chemical reactions occur. First, the paraffinic and i-paraffinic portions of the stream crack down to form light olefins. Second, the naphthenic portion is dehydrogenated to form cyclic or chain olefins. Some of these olefins may combine and rearrange to form aromatics, such as toluene and xylenes. Such aromatic growth is different from the aromatic alkylation pathway in typical methanol-to-gasoline (MTG) where highly methyl-substituted benzenes are normally the preferred products. It is known that toluene and xylenes are desirable for high octane, while durene (1,2,4,5-tetramethyl benzene) is not. The generation of additional desirable species, such as toluene and xylenes, is always a positive direction for octane enrichment. Besides, naphthenic components are known to be undesirable for high octane rating. In addition, iso-durenes are known to be bad actors for viscometric properties, as they increase the fuel viscosity. The conversion of undesirable naphthenes into desirable species, such as toluene and xylenes, is one of the most effective way to enhance octane and improve viscometric properties of fuel made from synthesis gas (synfuel). Besides aromatization, the acid zeolite catalyst has the capability for transalkylation, where methyl groups may be interchanged among aromatic moieties intra- or inter-molecularly. The zeolite-forming pathway is summarized in FIG. 1.

Zeolite-forming has been extensively studied by Zeosit and exercised in many refineries, located mostly in Eastern Europe and Russia. The economic evaluation has also been conducted in a comparison to other reforming technologies based on precious metals (Stepanov et al., Chemistry for Sustainable Development 13:505-518 (2005); Rovenskaja et al., Chem. Ind. 57(9):399-403 (2003); Erofeev et al., XVIII International Scientific Symposium in Honor of Academician M.A.Usov PGON2014). In contrast to Pt-reforming, zeolite-forming does not require the expensive catalysts and the hydrofining stages to remove sulfur and nitrogen species from the raw materials. The regeneration of Pt-based catalyst is difficult and not cost effective. Due to the light gas loss, zeolite-forming needs to be optimized between the recovery and efficiency in octane boosting. In other words, the use of zeolite-forming alone may not be a sufficient way to improve octane rating in synfuel.

Therefore there is a need to increase octane rating in synfuel without the drawbacks discussed above.

SUMMARY OF THE INVENTION

One aspect of the present invention provides a process which combines transalkylation, zeolite-forming, and aromatization (methanol-to-aromatics) in conjunction with a single recycle loop configuration in order to effectively promote the fuel quality, particularly octane rating. The process involves adding a step for enriching octane of the fuel coming from the single recycle loop process. Preferably, the enrichment step takes place in an octane enrichment reactor containing two different catalysts, a zeolite-forming/aromatization catalyst followed by a transalkylation catalyst. The final fuel product preferably has an octane of about 92 to about 112, more preferably about 95 to about 105, most preferably about 98 to about 101.

Another aspect of the present invention provides a process to produce high octane fuel. The process entails four sequential catalytic stages with intermediate heat exchange to provide the requisite temperature in each stage, but with no interstage separation. The unreacted gases from the fourth stage are recycled to the first stage after separation of the medium RON (research octane number) fuel from the unreacted gases in a condenser. The medium RON fuel is then lead to the octane enrichment reactor to increase the octane of the intermediate fuel.

The four sequential catalytic stages are detailed in U.S. Pat. No. 8,686,206 ('206 patent), which is incorporated herein by reference. The four reactor stages are connected in series, preferably interconnected with heat exchangers to adjust the temperature of the outflow of one stage to correspond to the desired inlet temperature of the next stage. Each stage may have one or more reactors in series or in parallel, loaded with the same catalyst. No separation or removal of intermediate product is made between the first to fourth stages. The first stage converts synthesis gas to methanol and water; the second stage converts a portion of the methanol to dimethylether; the third stage converts methanol and dimethylether to fuel products and heavy gasoline; and the fourth stage converts the heavy gasoline via hydrotreating reactions to additional fuel products.

A further aspect of the present invention provides another process to produce high octane fuel. The process entails three sequential catalytic stages with intermediate heat exchange to provide the requisite temperature in each stage, but with no interstage separation. The unreacted gases from the third stage are recycled to the first stage after separation of medium RON fuel from the unreacted gases in a condenser. The intermediate fuel is then lead to the octane enrichment reactor to increase the octane of the intermediate fuel.

The three sequential catalytic stages are detailed in U.S. patent application Ser. No. 14/566,233 ('233 application), filed Dec. 10, 2014, which is incorporated herein by reference. The process contains three reactor stages in series, preferably interconnected with heat exchangers to adjust the temperature of the outflow of one stage to correspond to the desired inlet temperature of the next stage. Each stage may have one or more reactors in series or in parallel, loaded with the same catalyst. There is no separation or removal of intermediate product. For gasoline synthesis, the first stage converts synthesis gas to methanol and water; the second stage converts a portion of the methanol to dimethylether; the third stage converts methanol and dimethylether to fuel products and heavy gasoline, and part of the third stage also converts the heavy gasoline components via hydrotreating and transalkylation reactions to fuel products.

Other aspects of the invention, including apparatus, devices, processes, and the like which constitute part of the invention, will become more apparent upon reading the following detailed description of the exemplary embodiments.

BRIEF DESCRIPTION OF THE DRAWINGS

The foregoing background and summary, as well as the following detailed description of the drawings, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION

The invention relates to systems and processes for improving octane for fuel produced from synthesis gas (syngas). The final fuel product has an octane rating of greater than about 92, preferably about 92 to about 112, more preferably about 95 to about 105, most preferably about 98 to about 101. As used herein "high RON fuel" or "high octane fuel" or the like refers to fuels having RON of greater than 92. In addition, the final fuel product has reasonable heat of combustion (greater than about 43 MJ/Kg) and a freezing point of less than −58° C.; and contains no lead, no multi-ring compound (only single ring compounds are present), less than about 15 ppm sulfur, and/or less than about 5 ppm nitrogen species.

Figure 2:
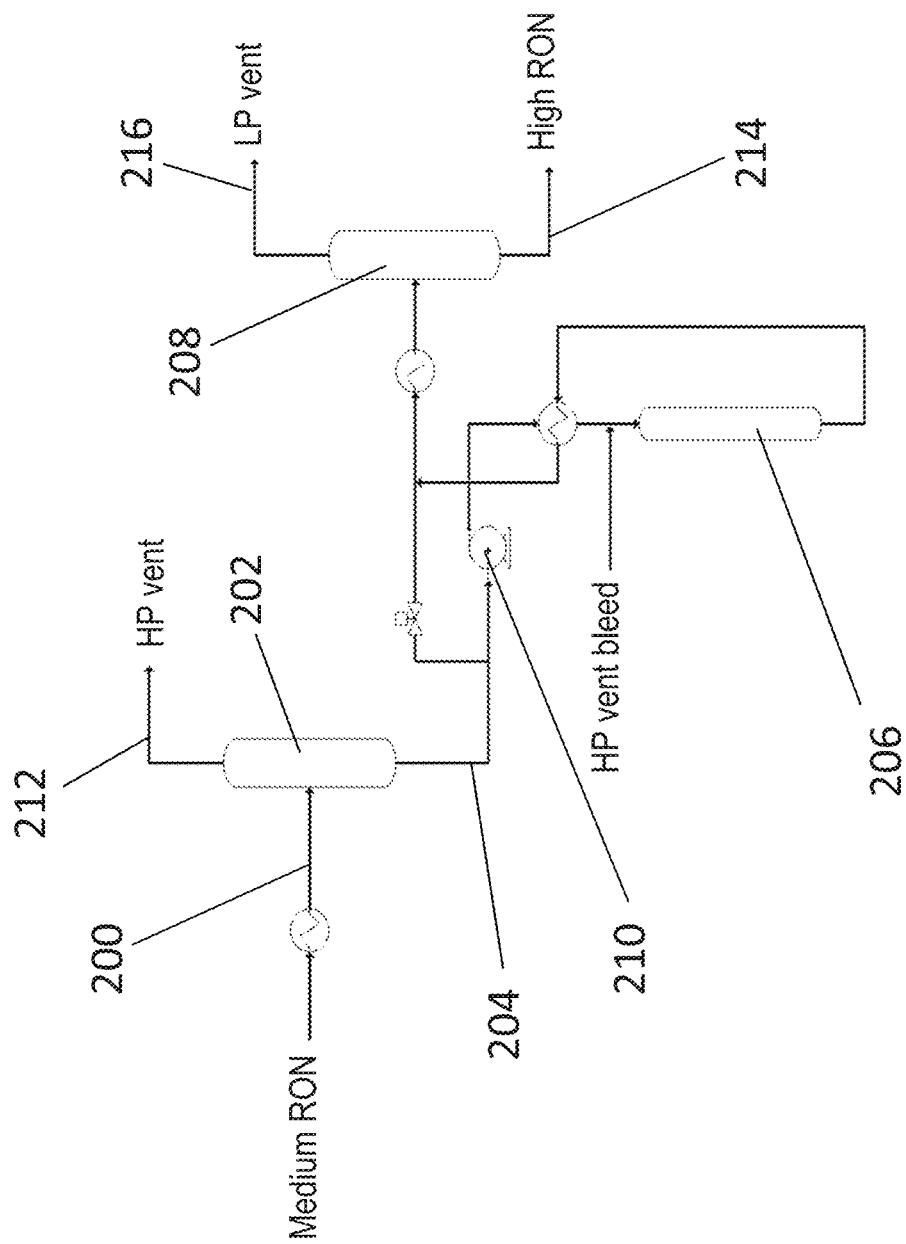
FIG. 2 is a schematic showing R5 of the present invention.

The system of the present invention provides a reactor system to produce high octane fuel from syngas. Fuel having medium research octane number (RON) (medium RON fuel) may be produced from the four reactors of the system (R1 to R4) as provided by U.S. Pat. No. 8,686,206 ('206 patent), which is incorporated herein by reference. The '206 patent provides a four-stage reactor (from R1 to R4) in a single recycle loop configuration to provide gasoline synthesis from synthesis gas (syngas) directly in a continuous fashion. That process involved four sequential catalytic stages, preferably with intermediate heat exchange, to provide the requisite temperature in each stage, but with no interstage separation (the process is also referred to herein as the "MTGH process"). The first reactor (R1) converts synthesis gas to principally methanol and some water. The product from the first reactor (R1), a vapor mixture of essentially methanol, water and unreacted synthesis gas, flows to a second reactor (R2). The second reactor (R2) converts a portion of the methanol to dimethylether. The product from R2, which essentially contains methanol, dimethylether, water and unreacted synthesis gas, flows via a conduit to a third reactor (R3). The third reactor (R3) converts methanol and dimethylether to fuel product (gasoline, jet fuel and/or diesel) and heavy gasoline. The product from R3 contains essentially fuel product ($C_5$-$C_8$ hydrocarbons, toluene, and xylene), heavy gasoline (>C8 aromatics) and water, with minor amounts of unreacted methanol and dimethylether and unreacted synthesis gas. This product flows to a fourth reactor (R4) to convert the heavy gasoline to a product containing the fuel composition with low heavy gasoline content, water, minor amounts of unreacted methanol and dimethylether and unreacted synthesis gas. This fuel composition can then be separated from the water, the light gases (including light paraffins ≤C4), and unreacted syngas using a separator 202, as shown in FIG. 2. The product from R4 may be led to the separator 202 via conduit 200. Other variations and specific embodiments of the MTGH process disclosed in the '206 patent are appropriate for the present invention. The fuel composition produced from the separator 202 may typically have an octane rating of about 84 to about 90, which is the same as the fuel produced in R4 (not including water and unreacted syngas). Fuel containing this octane rating is referred to herein as "medium RON fuel" or "medium octane fuel" or the like.

Alternatively, the medium RON fuel may be produced by the process disclosed in co-pending U.S. patent application Ser. No. 14/566,233 ('233 application), filed Dec. 10, 2014, which is incorporated herein by reference. This process contains three reactors, the first two reactors are identical to R1 and R2 of the MTGH process disclosed in the '206 patent (hence the first two reactors for this process is also referred to herein as R1 and R2). The third reactor (referred to herein as R3/4) is essentially combines R3 and R4 of the MGTH process into a single stage with the catalysts of R3 and R4 in the same reactor (R3/4). R3/4 converts methanol and DME to fuel product ($C_5$ to $C_8$ hydrobarbons, toluene, and xylene) and heavy gasoline (>$C_8$ aromatics), while concurrently and synergistically hydrotreating any non-preferred hydrocarbon products. The hydrotreatment reduces the heavy gasoline (trimethylbenzenes and tetramethylbenzenes) to produce the medium RON fuel, such as toluene, xylenes and $C_5$ to $C_8$ hydrobarbons, principally $C_5$ to $C_7$ hydrocarbons. R3/4 carries out both the hydrocarbon synthesis and hydrotreatment reactions in a single reactor. As such, R3/4 contains two different catalysts, one for hydrocarbon synthesis (converts methanol and dimethylether to fuel product (gasoline, jet fuel and/or diesel) and heavy gasoline) and one for hydrotreating the heavy gasoline to medium RON fuel product. Like the MGTH process, preferably intermediate heat exchangers are provided between the three reactors (R1, R2, and R3/4) to provide the requisite temperature in each stage, but no interstage separation is provided. As noted above for the product of R4, the product produced by R3/4 may also be led to the separator 202 to separate the fuel (medium RON) from the water, the light gases (including light paraffins ≤$C_4$), and unreacted syngas using a separator 202, as shown in FIG. 2. Other variations and specific embodiments of the process disclosed in the '233 application are appropriate for the present invention. Both the processes of the '206 patent and the '233 application, may produce medium RON fuel.

The catalysts used in the R1 and R2 are well known in the art from prior MTG processes. Appropriate catalysts for R-1 include, but are not limited to, $CuO/ZnO/Al_2O_3$, Zn—Cr and other bifunctional catalysts doped with certain elements can also carry methanol synthesis. Appropriate catalysts for R-2 in gasoline application include, but are not limited to, gamma-alumina, zeolites and other mesoporous materials can also carry methanol dehydration into dimethylether.

The catalyst used in R3 is a hydrocarbon synthesis catalyst that converts methanol and dimethylether to fuel product (gasoline and/or jet fuel) and heavy gasoline). Hydrocarbon synthesis catalysts are well-known in the art from prior MTG processes. Appropriate catalysts for R-3 include, but are not limited to ZSM-5, SAPO-34 and other MFI zeolites can also carry hydrocarbon synthesis.

The hydrotreating catalysts used in R4 include, but not limited to, certain larger pore zeolites and Group IX or X metal oxide (e.g. nickel oxide) catalyst on alumina reduced in the presence of hydrogen and carbon monoxide in the absence of sulfur. In certain embodiments, the catalyst can be Group IX or X metal oxide (e.g. cobalt oxide) catalyst combined with a Group VI metal oxide (molybdenum oxide) catalyst on alumina reduced in the presence of hydrogen and carbon monoxide and in the absence of sulfur. A specific example of the catalyst include unsulfided cobalt molybdate on alumina or atomic nickel on alumina, the reduction, if any, being carried out in the presence of synthesis gas. Sulfiding the catalyst surface is not necessary but catalytic reduction using either a $H_2$ flow or a mixture of $H_2$ and CO under operating temperature is desirable. Temperature of the fourth stage ranges from 120 to 230° C. (248 to 446° F.) depending on the catalyst used, with the preferred temperature being about 150-180° C. (302 to 356° F.). These temperatures are surprisingly lower than 232 to 427° C. (450 to 800° F.) disclosed by Garwood (U.S. Pat. No. 4,304,951) for treating a 200-400° F. bottoms fraction. We ascribe this valuable difference in temperature and the more desirable product mix to treating the whole product from the fuel forming step in the presence of synthesis gas instead of a bottoms fraction with principally hydrogen. We also ascribe this surprising result to using unsulfided catalysts, unlike Garwood that teaches by example that mixed oxide catalysts need to be sulfided. Han et al. (U.S. Pat. No. 4,973,784) teaches the use of zeolites for treating the durene containing product in the presence of substantial partial pressure of hydrogen producing undesirable benzene. Our novel process does not produce benzene. Still in another variation, Chester et al. (U.S. Pat. No. 4,387,261) propose treating the entire product from the fuel forming stage, but preferably a heavy fraction thereof, using ZSM-12, preferably impregnated with platinum, an expensive metal, at elevated temperatures and pressures to dealkylate durene to form xylene, toluene, benzene and undesirable light gases such as $C_2$ and $C_3$ hydrocarbon. The present process is clearly superior in that it does not produce light gases in the treating stage (stage 4). Still in another example, Dwyer et al. (U.S. Pat. No. 4,347,397), showed that treating the whole or bottoms product from the fuel producing stage with zeolites principally isomerizes the durene to other tetramethylbenzenes, thereby, producing less desirable heavy product than the present process. The preferred transalkylation catalyst is Y-zeolite (e.g. USY), beta-zeolite, or combinations thereof. Particularly preferred Y-zeolites are those with silica to alumina ratios (SAR) of about 10 to about 40.

R3/4 contains two different catalysts, one for hydrocarbon synthesis (used in R3) and one for hydrotreating the heavy gasoline to fuel product (used in R4). Preferably, R3/4 contains ZSM-5 as the hydrocarbon synthesis catalyst and a zeolite catalyst, preferably Y-zeolite, as the hydrotreating catalyst. The zeolite catalyst is used as a hydrotreating catalyst, in that it acts to reduce durene and other heavy gasoline components in the mixture through disproportionation, isomerization, and transalkylation across benzene molecules. The hydrocarbon synthesis reaction that occurs in R3/4 results in a mixture principally comprised of fuel product (C4-C8 hydrocarbons, toluene, and xylene), heavy gasoline (≥C8 aromatics), water, and unreacted synthesis gas. The heavy gasoline and highly substituted aromatics in this mixture react in the presence of the zeolite-based catalyst, preferably Y-zeolite, in R3/4 to produce the preferred fuel, such as C4-C8 hydrocarbons, toluene, and xylene. The catalyst bed is preferably a mixture of ZSM-5 and zeolite at levels that are optimized based on operation parameters such as the recycling rate in the system and the environmental temperature in R3/4. The synergy between the ZSM-5 hydrocarbon synthesis catalyst and the zeolite hydrotreatment catalyst in R3/4 results from the formation of certain intermediates generated by the zeolite catalyst that serve as co-feeding components promoting performance cycles of hydrocarbon pools. Thus, the hydrotreatment portion feeds back positively to the hydrocarbon synthesis, improving reaction efficiency.

Referring to FIG. 2, the liquid medium RON fuel coming from the condenser 202 flows into an octane enrichment reactor (R5) 206, preferably using a liquid pump 210 via conduit 204. R5 206 is located downstream from the condenser 202 but upstream of a stabilizer (or second condenser) 208, so that the high RON fuel coming from R5 206 can be condensed again in the stabilizer 208. The high RON fuel may be collected at the bottom of the stabilizer 208 in stream 214. At the top of the stabilizer 208, light flue gas (≤$C_4$) is vented through stream 216. In an embodiment, a portion of the gas from the top of the condenser 202 (which is rich in $H_2$ and typically vented through stream 212) may be directed into R5 206 as a carrier gas. In that case, the carrier gas makes up about 5 to about 15 weight %, preferably about 10%, of the total feed into R5 206. The amount of carrier gas used is calculated to achieve a $H_2$ concentration in R5 206 of about 20 to about 50 molar % (based on the total gas in R5 (fuel and carrier gas)).

R5 206 is a catalytic reactor and contains at least two catalysts: one for zeolite-forming/aromatization and one for transalkylation. Preferably, both catalysts require similar operation conditions (including space velocity, temperature, and pressure). In an exemplary embodiment, the two catalysts are configured as two separate layers in R5 206. For example, the two layers are configured as two distinct beds in R5 206 to provide a zeolite zone and a transalkylation zone. Preferably, the medium RON fuel, from the condenser 202, first contacts the zeolite-forming/aromatization catalyst, preferably at the top of R5 206, before proceeding to the transalkylation catalyst, preferably at the bottom of R5 206. Alternatively, the catalysts may be mixed together in a single bed. R5 206 is preferably operated at a temperature of about 350 to about 480° C., preferably about 380 to about 450° C., a pressure of about 5 bar to about 35 bar, preferably about 10-25 bar, and/or a weight hourly space velocity (WHSV) of about 1 to about 5 $hr^{-1}$, preferably about 2 to about 4 $hr^{-1}$.

Figure 1:
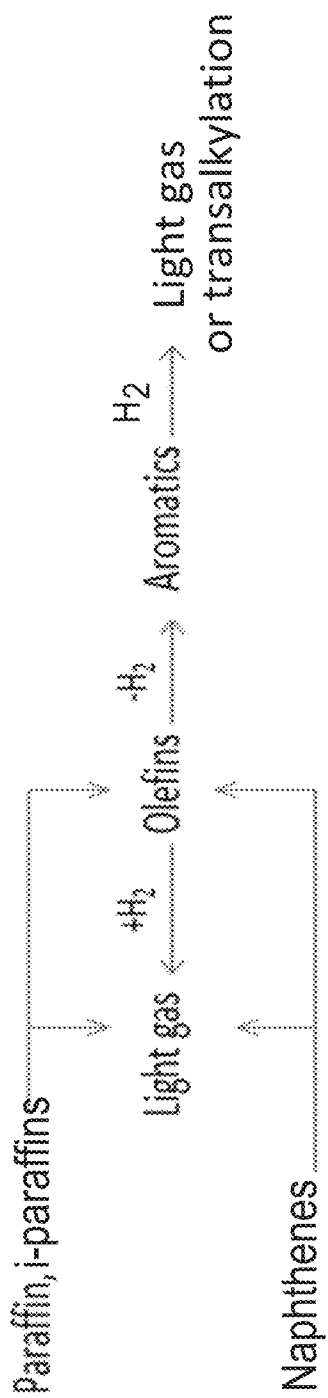
FIG. 1 is a chart showing the zeolite-forming pathways.

In order to match the operation conditions, in certain embodiments, modification of zeolite-forming/aromatization catalyst may be necessary. Modified zeolite with certain metal doping or impregnation is used as the top layer catalyst in this reactor. The metal may be, but is not limited to, alkali and alkali earth metals, such as Mg, Ca, K, etc.; transition metals, such as Zn, La, etc., or combinations thereof. The reactions shown in FIG. 1 may be conducted in the top layer of R5 where certain i-paraffins and naphthenes are effectively converted into aromatics to increase octane. Test results also show that the octane lowering species, such as iso-hexanes, iso-heptanes and methyl- and/or di-methyl cyclohexanes, substantially decrease (weight percentage may drop more than 40%), while octane boosters, such as toluene and xylenes, increase about 3-6 times in weight amounts. Such change leads to a significant boosting in octane rating. The increase of the research octane number (ΔRON) may be in the range of about 10-12. The zeolite-forming/aromatization catalyst may be, but is not limited to, ZSM-5, ZSM-11, mordenite, chabazite, or combinations thereof, with ZSM-5 having an SAR of about 25 to about 120 being the preferred catalyst.

The transalkylation catalyst used in the bottom layer of R5 may be the same catalyst used in R4 as described above. A zeolite based transalkylation catalyst is preferably used in the bottom layer of R5 to further inhibit durene formation in order to maintain a good viscometric property of the high RON fuel product. A typical example is, e.g., the reaction between xylene and durene where the immediate products are toluene and trimethylbenzenes. The final high octane product (high RON) may be condensed in a stabilizer 208 to separate high RON fuel from light flue gas ($C_4$).

The present invention provides an extension of the system of the '206 patent or the '233 application to produce a continuous process for producing high RON fuel by coupling a zeolite-forming and transalkylation reactor (R5) with the MTGH process or the process of the '233 application. Most importantly, the transalkylation function of R4 is also included and coupled into R5 in order to continuously improve product quality. R5 provides an integrated octane enrichment module for the process of the '206 patent or the '233 application.

During the octane enrichment, certain light gas is generated and the recovery of the high octane product will never reach 100%. In general the recovery value varies from about 50% to 90% of the feed, depending upon the operation conditions (pressure and temperature) and the modification of the catalyst in R5. However, the decomposed light species within the vent gas from the stabilizer may be directed into the upstream reformer that further reacts with the steam to generate syngas through the reforming process.

The major difference between the standard zeolite-forming and the operation of the present invention may be categorized in the following few points: (1) the present invention is a continuously integrated system where the vent gas derived from R5 may be fed into reformer as a single loop which is not performed with other zeolite-forming methods; (2) The use of Y or beta zeolites in the lower layer of R5 is an effective way in combining transalkylation function with zeolite-forming so that the durene level remains low; (3) due to the recycle in the single-loop, the present invention is operated under $H_2$-rich (preferably about 20 to about 50 molar % (based on the total gas in R5 (fuel and carrier gas)) condition where the hydrogen presence assists the decomposition of highly alkylated aromatics through hydrocracking (it is known that the highly alkylated aromatics are precursors for coke formation which adversely impact the catalyst lifetime), which reduce catalyst degradation; and (4) the use of transition metal or alkali earth metal doping or impregnation on the zeolite catalysts in R5 allows for significantly improvement in aromatic enrichment which dramatically improve the recovery or minimize the loss during zeolite-forming.

Without further description, it is believed that one of ordinary skill in the art can, using the preceding description and the following illustrative examples, make and utilize the catalyst of the present invention and practice the claimed methods. The following examples are given to illustrate the present invention. It should be understood that the invention is not to be limited to the specific conditions or details described in the examples.

Example 1

In this example, three zeolite based catalysts with different acidity were tested using a pilot reactor. The amount size for the gasoline quantity of the pilot reactor is in the range of about 1 Kg/hr. Basically a relatively low octane fuel (RON=81, density ρ=0.705 g/ml) was injected into the reactor with a feeding rate of 7-10 g/minute. The system pressure of the pilot unit was about 10 bars and the reactor temperature was varied from 350° C. to 420° C. The temperature change was aimed to select the optimal window for highest recovery and the best octane enhancement. After the conversion, the octane increase (ΔRON) and the composition of the final product were evaluated by a PONA analyzer. Both the ΔRON and the recovery % values are plotted in FIG. 3. The zeolite acidity is characterized by the silica-to-alumina ratio (SAR). The acidity trend is as follows: catalyst-A (SAR=60)>catalyst-B (SAR=90)>catalyst-C (SAR=120).

Figure 3:
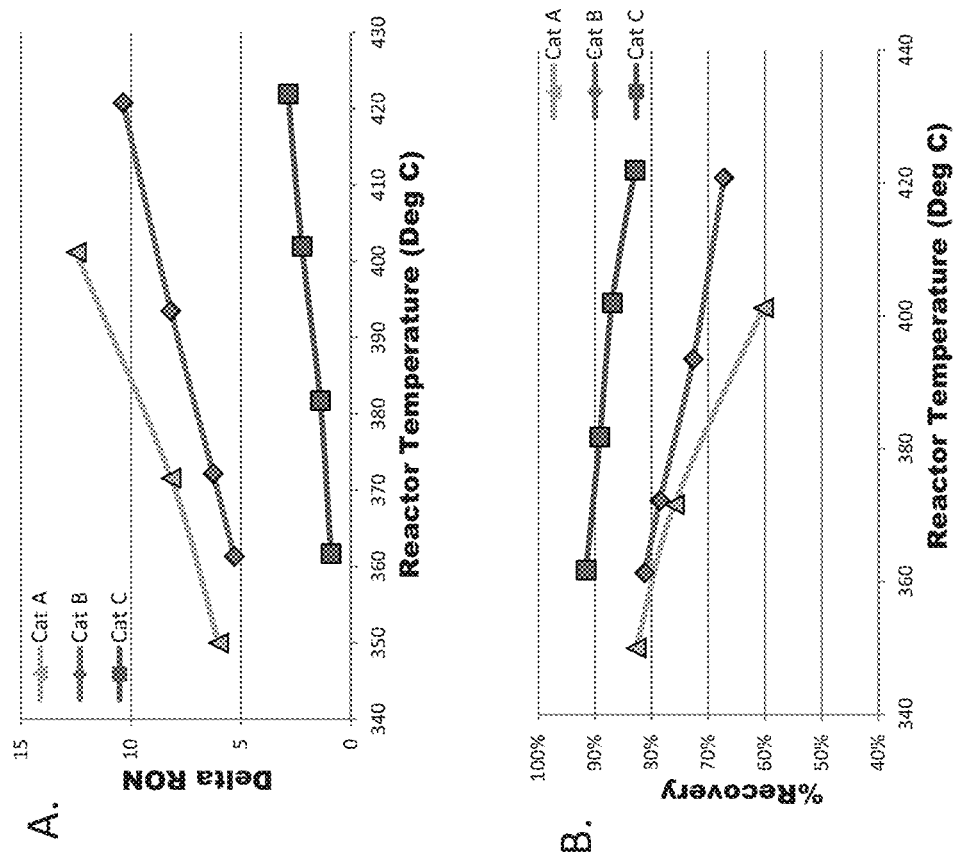
FIG. 3 are graphs showing A) octane enhancement (ΔRON); and B) the corresponding recovery % of the pilot test using catalysts with different ratios of SAR.

As shown in FIG. 3, ΔRON increases with the acidity of the catalyst; the more acidic the catalyst, higher the ΔRON. At T=400° C., the most acidic catalyst, catalyst-A, generated an octane enhancement of nearly 12 octane units which was significantly larger than the 8 for catalyst-B and 2 for catalyst-C. However, the recovery % followed a completely opposite trend of catalyst-A (60%)<catalyst-B (71%)<catalyst-C (88%). The composition information reveals the chemical pathways for such octane increase. Take catalyst-A as an example (Table 1), the iso-paraffinic portion drops more than 55% and the naphthenic part drops more than 42%. The aromatic portion, as well as the olefinic portion, increases more than 50% from the original fuel to the final product. Among the aromatics, the amounts of toluene and xylenes (octane boosters) increase dramatically. Apparently, certain iso-paraffinic and naphthenic compounds may have been converted into aromatics following the route described in the equations of FIG. 1.

TABLE 1

|  | The original synfuel | The fuel after zeolite-forming |
|---|---|---|
| Density (g/ml) | 0.715 | 0.814 |
| i-P (iso-paraffins) | 50.7% | 21.3% |
| P (paraffins) | 5.1% | 5.5% |
| A (aromatics) | 28.6% | 58.1% |
| O (olefins) | 1.1% | 3.1% |
| N (naphthenes) | 12.3% | 7% |
| RON | 81 | 93.5 |

It is apparent that the octane enhancement of synfuel product is inversely proportional to the yield (recovery %); hence, the larger the ΔRON, the lower the recovery value. Please note all catalysts used in the example of FIG. 3 were plain zeolite samples with different SAR values. When the plain catalyst was modified with transition or alkali earth metal doping, the potency of recovery may significantly be increased.

Example 2

Figure 4:
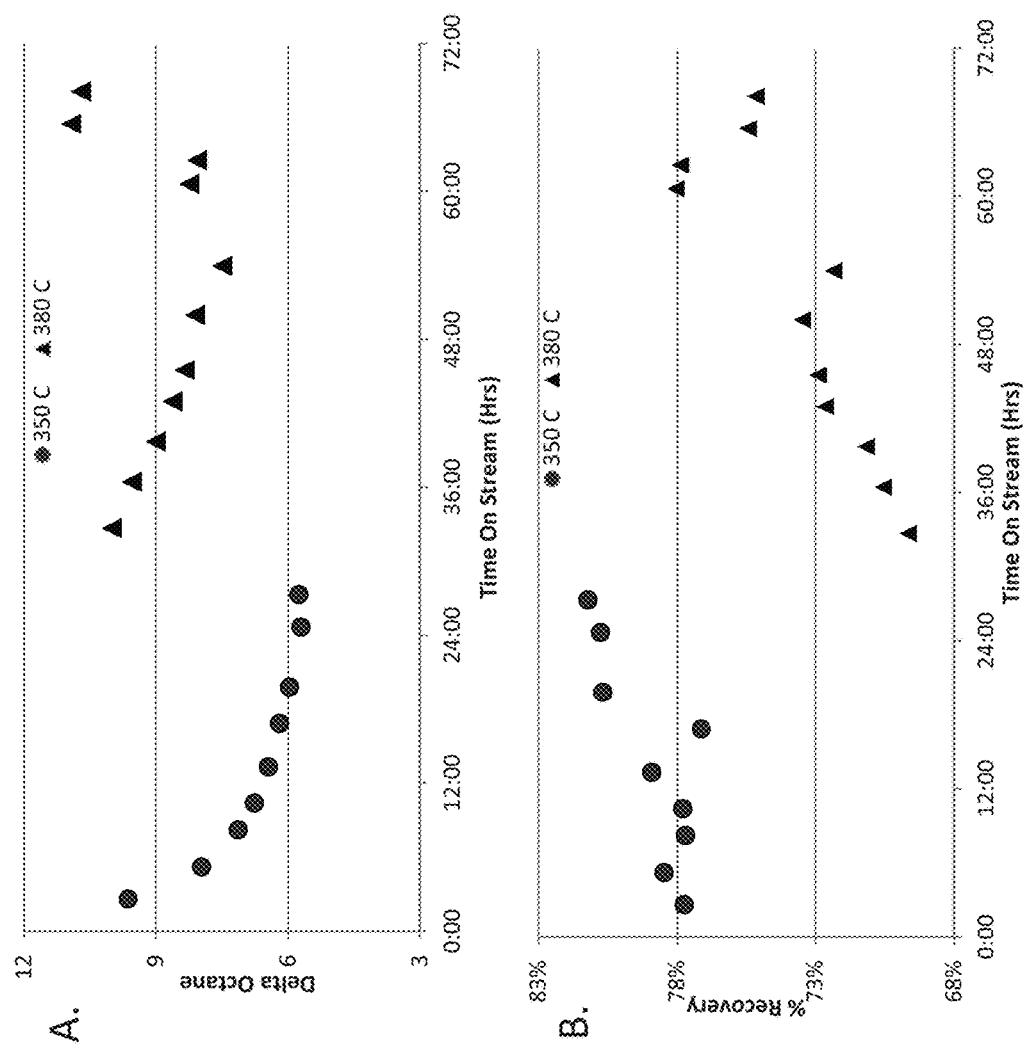
FIG. 4 are graphs showing zeolite-forming lifetime evaluation using two-layer configuration in pilot reactor: A) ΔRON as a function of time on stream; and B) % recovery as a function of time on stream.

In this example, we evaluated the catalyst lifetime. Two zeolite based catalysts were layered in pilot reactor to test the concept of R5. The catalyst in the top layer performs zeolite-forming/aromatization for octane enrichment (ZSM-5 type catalyst); and the catalyst in the bottom layer performs transalkylation to reduce durene formation (USY type catalyst). Both ΔRON and the recovery % are plotted in FIG. 4 against the time on stream. At the initial temperature of 350° C., the ΔRON followed an exponentially decaying function from 9.6 to 5.5 after 35 hours. As the ΔRON leveled off around 5.8, we raised the temperature of R5 from 350° C. to 380° C., and ΔRON jumped back to 10. Following the exponential decay for another period of 30 hours or so, the ΔRON leveled again around 7.5. The temperature is again raised to 400° C., and ΔRON jumped rapidly to 10.5.

If the temperature is continuously raised following such sawtooth pattern from 380° C. to 450° C., the overall operation time can be extended to more than 150 hours before any significant degradation of the catalyst is observe. Such extension in operation time provides additional benefit to the standard zeolite-forming operation. Apparently, the benefit comes from the combination of transalkylation function with the zeolite-forming function introducing more variables to adjust the optimum operation conditions. The transalkylation in the bottom part of R5 contributes to octane enrichment. The transalkylation is also a function of operation temperature (the higher the temperature, the more potent in methyl rearrangement). The initial ΔRON values, 9.6 at 350° C., 10 at 380° C., and 10.5 at 400° C., seem to increase slightly with the reactor temperature. The leveling off temperatures, 5.8 at 350° C. and 8 at 380° C., also follow an increasing trend. With the presence of $H_2$, the lifetime is expected to become even longer. As will be discussed in the next section, the hydrocracking of certain high alkyl-substituted aromatics which are known to be coke precursors play important roles in lifetime extension.

Example 3

In our single-loop systems (the '206 patent or the '233 application) with the recycling from the vent gas of condenser to R1, the system pressure is high and the gas stream is rich in $H_2$. As mentioned above, the hydrogen content is expected to have impact on catalyst lifetime. In this example, we evaluated the hydrogen impact on octane enrichment. To do so, we compared the microreactor performance of a typical zeolite-forming/aromatization catalyst (20 g with SAR-120) with a feed of low octane fuel (RON=81.5) under different gases, $N_2$ only, $N_2/H_2$ mixture (50:50), and $H_2$ only (with the total flow of 2000 sccm). The operation condition was 400° C. and system pressure P=62 bars. The results are listed in Table 2.

TABLE 2

|  | Original low-RON fuel | Zeolite-forming under N2 | Zeolite-forming under N2/H2 | Zeolite-forming under H2 |
| --- | --- | --- | --- | --- |
| C3 | 0.00 | 1.11 | 0.63 | 0.62 |
| C4 | 0.02 | 2.37 | 2.17 | 3.26 |
| C5 | 15.04 | 2.03 | 3.47 | 6.90 |
| C6 | 26.29 | 1.59 | 1.99 | 3.69 |
| C7 | 13.88 | 0.33 | 0.26 | 0.67 |
| Paraffin | 5.17 | 3.53 | 3.25 | 3.28 |
| i-Paraffin | 55.95 | 6.31 | 7.87 | 12.94 |
| Olefin | 1.69 | 5.32 | 4.12 | 2.69 |
| Naphthene | 15.10 | 4.95 | 4.73 | 4.44 |
| Aromatic | 20.75 | 69.38 | 70.46 | 70.57 |
| C15+/unknown | 13.32 | 10.51 | 9.58 | 5.08 |
| toluene | 0.62 | 17.33 | 15.40 | 12.05 |
| m-xylene | 2.44 | 11.21 | 10.97 | 10.91 |
| p-xylene | 1.07 | 3.34 | 3.34 | 3.38 |
| o-xylene | 1.01 | 4.63 | 4.56 | 4.57 |
| 1,2,4-TMB* | 5.85 | 5.07 | 5.75 | 7.27 |
| 1,3,5-TMB* | 0.41 | 1.70 | 2.44 | 3.01 |
| 1,2,3-TMB* | 0.32 | 0.93 | 1.04 | 1.22 |
| durene | 2.97 | 5.06 | 7.23 | 8.55 |
| i-durene | 3.12 | 6.84 | 9.86 | 11.63 |
| Octane (RON) | 81.50 | 96.00 | 95.80 | 98.90 |

*TMB = trimethyl benzene

Figure 5:
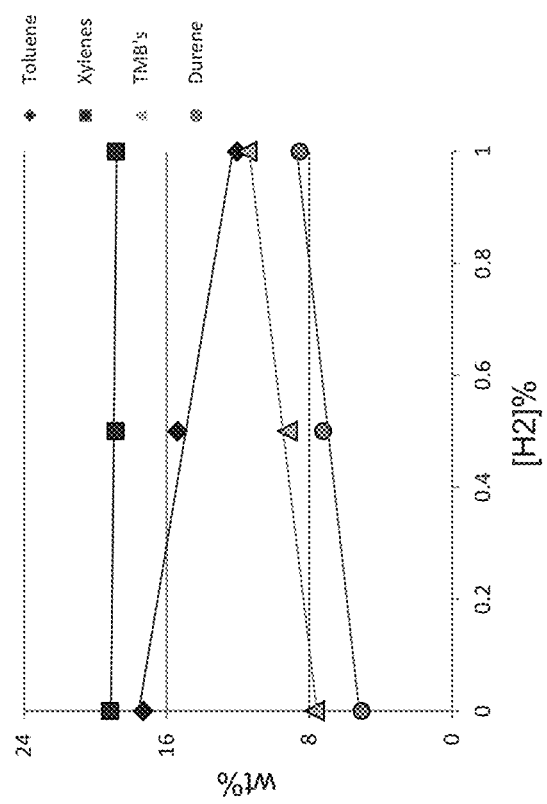
FIG. 5 is a graph showing the dependence of aromatics on $H_2$ concentration.

As shown in Table 2, zeolite-forming improved the content of toluene (from 0.62% to 17.33%, nearly ×28) and xylenes (from 4.52% to 19.18%, nearly ×4). It also slightly increased the content of TMB (from 6.58% to 7.7%, ×1.1) and durene (from 6.09% to 11.9%, only ×1.7). The increased concentration for light aromatics (octane boosters) were significantly higher than the heavy aromatics (octane suppressors). This was the reason that ΔRON is still in the positive trend even at high $H_2$ concentration. The concentrations of various fuel components were quite sensitive to $H_2$ content. The increase of the paraffinic components ($C_5$-$C_7$) may have followed an increasing rate of a certain chemistry involving hydride transfer or hydrocracking which may be related to the excess of $H_2$. This trend can be seen in Table 2. The $H_2$ concentration trends with aromatics, as shown in FIG. 5, may be related to hydrocracking of certain heavy alkylated aromatics (C12+). As the $H_2$ concentration was increased, both durene and TMBs (trimethylbenzenes) concentrations increased slightly while the toluene decreased. The xylene concentration was somewhat insensitive to $H_2$ concentration.

We observed that an exothermic reaction occurs in the reactor when $H_2$ is present. As we shut off the carrier $H_2$, a sudden drop of reactor temperature by 5-6° C. was measured by the bed thermocouple. Hydrocracking processes can be attributed to such exothermic behavior. The zeolite-forming in R5 may favor the formation of certain heavy alkylated aromatics ($C_{15+}$) which could crack down to form lighter species including durene and TMBs under $H_2$ rich condition. This can be seen in Table 2 where the concentration of $C_{15+}$/unknown decreased with $H_2$. These $C_{15+}$/unknown species are believed to be coke precursors. The presence of $H_2$ assisted in the reduction these coke precursors. Owing to the reduction coke precursors by $H_2$, the $H_2$ rich condition in the system brought additional benefit in extending catalyst lifetime. Based on our pilot operation, we do not need to regenerate zeolite catalyst for more than seven thousand hours. In other words, the lifetime of our catalyst can significantly be extended.

Example 4

This example verified the effectiveness of transalkylation in R5. The transalkylation involved intermolecular/intramolecular methyl rearrangement or disproportionation of methyl-substituted aromatics so that the highly methyl-substituted aromatics, such as durene, can be reduced. The main purpose of transalkylation was to reduce unwanted durene and i-durene in the synfuel product.

To carry out transalkylation evaluation, a reference solution (12.1% durene in toluene solution) was used. This liquid solution was continuously injected (at a rate of 0.7 ml/min or 42 ml/hr) into a microreactor containing 18 g of s USY catalyst (through a HPLC pump) heated under the proper temperature. The pressure and temperature of the microreactor were maintained at 5 bars and 350° C., respectively. An amount of 2000 sccm H₂ as carrier gas was flown to match the condition favored the methylation mechanism. The product coming out of microreactor was cooled down by a Peltier chiller; and the condensed liquid was analyzed by PONA for composition variation. The results are shown in FIG. 6.

Figure 6:
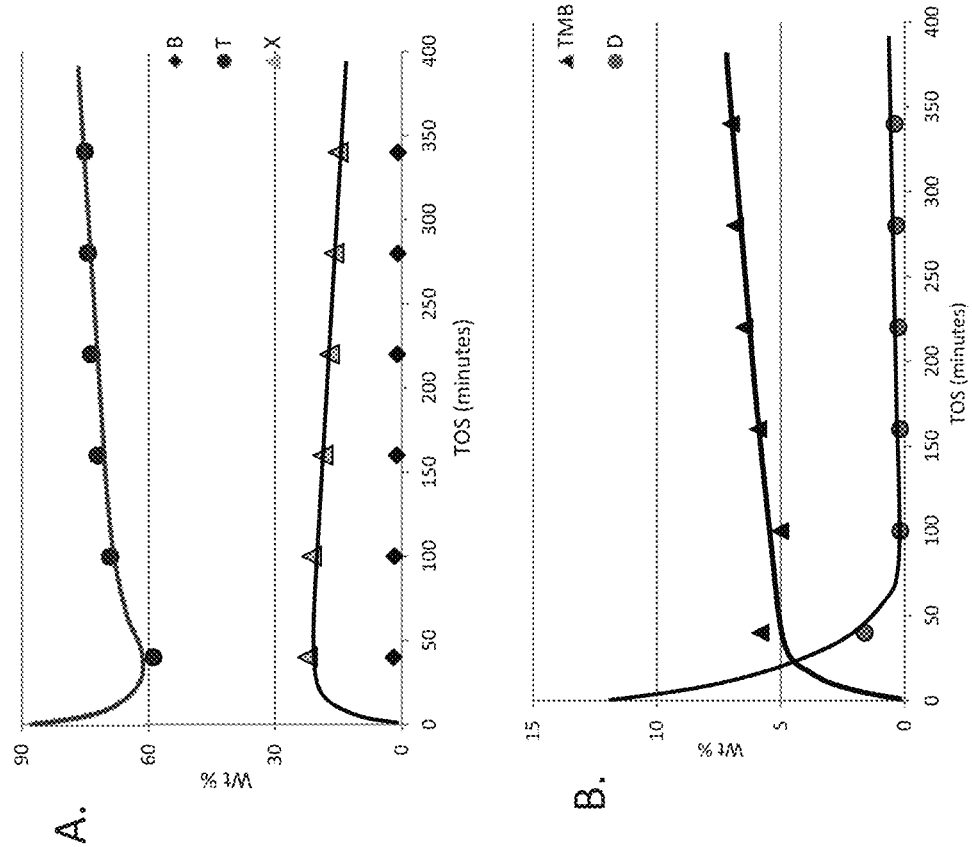
FIG. 6 are graphs showing transalkylation of the reference solution (12.1% wt durene and 87.9% wt toluene) as a function of time on stream (TOS): A) toluene (T), benzene (B), and xylene; B) durene and trimethyl benzenes.

As shown in FIG. 6, the concentration of toluene (T) dropped rapidly from its original 87.9% wt. to 60% in the first hour and then gradually increased towards 70% after 2 hr. (FIG. 6A). The initial drop was due to the initial high activity of transalkylation of the equation T+D→X+TMB (where X, D, and TMB stand for xylenes, durene, and trimethylbenzenes, respectively), while the later slowly increasing portion can be attributed to the gradual degradation of transalkylation where the activity degrades with time. The durene (D) concentration also dropped rapidly from its original 12.1% to 0.1% in the first 1.5 hr. and then gradually increased to 0.3% at after 3.75 hr. (FIG. 6B). The decay of reactivity was a measure of catalyst degradation. The xylene concentration followed a rough mirror image to toluene (FIG. 6A), while the TMB growth followed a mirror image to durene (FIG. 6B). Certain level of benzene (B) can also be seen (FIG. 6A), suggesting the possibility of the reaction T+T→B+X.

Figure 7:
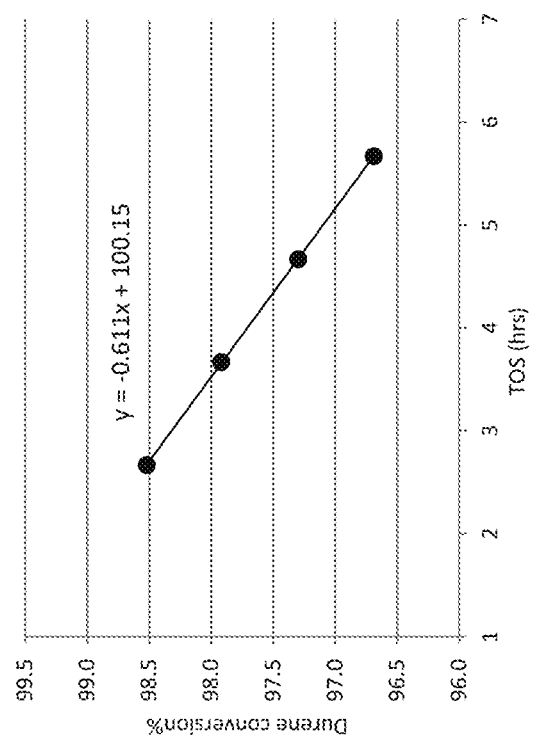
FIG. 7 is a graph showing the use of the decay rate of durene as an indicator for catalyst degradation.

The gradual decrease of the transalkylation activity may be used as an indicator of catalyst reactivity in terms of its durene reduction capability. As shown in FIG. 7, the drop in durene conversion followed a nearly linear function with time. Although both efficacy decreases in durene and toluene may be used to indicate the degradation, the quantification of durene was more reliable, because toluene was in excess in the reference solution. Besides, the growth of xylene seemed to be more quantitative than the growth of TMBs.

Another way to look at transalkylation was to compare molar ratios among isomers such as i-durene/durene and p-xylene/o-xylene. The thermal equilibrium values for these ratios were i-durene/durene=1.27 and p-xylene/o-xylene=0.8. When the catalysts were not active, these ratios would be deviated from their equilibrium values. As the catalyst reactivity is increased, the ratios would become closer to the equilibrium values. The ratio values following the reaction time sequence are listed in Table 3. It was interesting to note the transalkylation capability for xylenes was weaker than that for durene. Up to 2.8 hr., the p-xylene/o-xylene ratio had not yet reached equilibrium, while the i-durene/durene ration had already reached 1.27 after 2 hr. Based on thermal equilibrium, the distribution of xylene should follow a trend of [m-xylene]>>[o-xylene]>[p-xylene]. Any deviation from this trend could reflect an additional intramolecular isomerization chemistry.

TABLE 3

| Time (minute) | 40 | 80 | 120 | 160 | 202 | 225 |
|---|---|---|---|---|---|---|
| i-durene/durene | 1.00 | 1.16 | 1.26 | 1.28 | 1.27 | 1.27 |
| p-xylene/o-xylene | 0.70 | 0.71 | 0.72 | 0.74 | 0.80 | 0.82 |

The percentage change of durene conversion can be derived from the rate changes of durene following the reaction time, as shown in FIG. 7, and the decay rate for the USY zeolite catalyst was determined to be −0.611%/hr. This decay rate can be used as an indicator to evaluate the catalyst degradation behavior for various transalkylation catalysts. A database may be built to cover not only the plain catalysts, but also the modification ones with metal doping.

Example 5

Metal doping in zeolite is known to be helpful in the methanol-to-aromatic (MTA) process. Transition metals, including those in the Lanthanide series, are commonly used to modify the catalyst potency. This example verified the addition of zinc and ruthenium elements to improve zeolite-forming/aromatization capability. In this case, 1-3% Zn and trace amount of Ru were added onto a typical ZSM-5 catalyst through a typical ion-exchange technique. A fixed amount of reference fuel with known RON was injected into the microreactor containing 10 g of catalyst operated under 370° C. and 10 bars. After a fixed reaction time, fuel samples were collected for PONA analysis. Both ΔRON and recovery % were compared and listed in Table 4.

TABLE 4

|  | Plain catalyst | 1% Zn—Ru/ZSM-5 catalyst | | |
|---|---|---|---|---|
| LHSV (hr⁻¹)* | 2.0 | 1.35 | 1.35 | 1.35 |
| Temperature (° C.) | 370 | 370 | 400 | 430 |
| Pressure (bar) | 10 | 3 | 3 | 3 |
| H₂ (sccm) | 250 | 0 | 0 | 0 |
| N₂ (sccm) | 250 | 600 | 600 | 600 |
| Aromatics (%) | 61.88 | 55.87 | 64.65 | 75.28 |
| p-xylene/xylenes (mol %) | 20.6 | 21.1 | 19.2 | 18.3 |
| Recovery % | 59.7 | 65.42 | 62.32 | 62.23 |
| RON | 95 | 95.5 | 99.9 | 103.3 |

*LHSV = liquid hourly space velocity

At 370° C., there was no obvious improvement in octane increase. However the recovery seemed to improve to some extent. The temperature may be too low for effective zeolite-forming/aromatization. As the reactor temperature was raised, the benefit of metal modification can be clearly seen, as shown in the right three columns of Table 4. The operation under 430° C., 3 bar, LHSV=1.35 hr⁻¹ using N₂ as a carrier gas appeared to be a good practice where the ΔRON was high and the recovery % was reasonable.

Example 6

In this example a relatively large pilot unit was used to test the combination concept of zeolite-forming/aromatization and transalkylation in R5. The generation rate of gasoline product in this pilot unit was 5 gal/hr. The R5 unit was installed after the condenser where the raw gasoline product was collected but before the stabilizer where the light gas within the raw gasoline product was stripped to improve the vapor pressure (RVP) of the product. The configuration was as depicted in FIG. 2.

A medium-octane STGH fuel sample was firstly collected in the fuel tank. The composition of this fuel is shown in Table 5 as "original feed" fuel. The engine octane number (PONA simulated RON) for this original fuel was 90.1. The original fuel was then fed into the reactor to perform zeolite-forming/aromatization using ZSM-5 catalyst (top zone) followed by transalkylation by USY catalyst (bottom zone). Four conditions were run: condition-1 (both top and bottom zones are in 420° C.), condition-2 (both top and bottom zones are in 400° C.), condition-3 (top zone at 400° C., bottom zone at 420° C.), and condition-4 (top zone at 400 C, bottom zone at 440 C). Table 5 also shows the composition of the fuel resulting of each of the four conditions.

TABLE 5

| | Original feed | Condition-1 | Condition-2 | Condition-3 | Condition-4 |
|---|---|---|---|---|---|
| Temperature (° C.) | | 420 | 400 | 420 | 440 |
| WHSV | | 3 | 3 | 3 | 3 |
| Appearance | green | dark yellow | yellow | dark yellow | dark yellow |
| Density (g/ml) | 0.702 | 0.7779 | 0.7724 | 0.7681 | 0.758 |
| Paraffins | 8.6364 | 5.8502 | 6.8566 | 7.3277 | 7.7374 |
| I-paraffins | 55.4037 | 17.6138 | 27.2548 | 28.6104 | 30.3625 |
| Olefins | 0.9534 | 0.7666 | 1.0612 | 1.1737 | 1.4778 |
| Naphthenes | 4.8059 | 1.9903 | 2.3948 | 2.3587 | 2.3458 |
| Aromatics | 29.3499 | 67.254 | 57.3383 | 56.2199 | 54.0079 |
| benzene | 0.1501 | 3.0633 | 1.8274 | 1.6648 | 1.5513 |
| toluene | 2.3634 | 15.4353 | 11.1065 | 10.4838 | 9.8283 |
| o-xylene | 2.279 | 5.3292 | 4.4171 | 4.3510 | 4.2403 |
| m-xylene | 5.1571 | 13.4087 | 11.0391 | 10.6866 | 10.2182 |
| p-xylene | 2.1328 | 3.9112 | 3.6659 | 3.6935 | 3.7201 |
| TMB | 11.283 | 15.1053 | 13.7358 | 13.7226 | 13.4286 |
| durene | 1.4788 | 1.6629 | 2.1299 | 2.0413 | 1.9646 |
| i-durene | 1.9618 | 2.227 | 2.8106 | 2.7329 | 2.6763 |
| Total C15+ | 0.3909 | 3.6446 | 2.6104 | 2.2334 | 2.0141 |
| Unknowns | 0.4598 | 2.8806 | 2.4784 | 2.0709 | 2.0545 |
| P/A(wt) | 2.18 | 0.35 | 0.59 | 0.64 | 0.71 |
| P/A(molar) | 3.12 | 0.53 | 0.89 | 0.97 | 1.06 |
| D/i-D | 0.75 | 0.75 | 0.76 | 0.75 | 0.73 |
| Tot-xylenes | 9.5689 | 22.6491 | 19.1221 | 18.7311 | 18.1786 |
| D + i-D | 3.4406 | 3.8899 | 4.9405 | 4.7742 | 4.6409 |
| simulated RON | 90.1 | 102.3 | 98.8 | 100.1 | 99.8 |

*P = paraffin;
**A = aromatic; and
***D = durene

As shown in Table 5, the high octane rating can be partly attributed to the increase in octane boosters, including toluene and xylenes. Naphthenes, octane suppressors, were substantially reduced. By looking at the redistribution of aromatics, the heavy alkylated aromatics, such as durene and i-durene, were still high. These heavy alkylated benzenes are known to be octane suppressors. Coupling of transalkylation to zeolite-forming is expected to further improve the fuel quality by reducing the heavy alkylated aromatics. Regardless, relatively high engine octane numbers had been obtained, from 98 to 102.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A process for producing a high octane fuel comprising the step of
   passing a feed stream containing a medium octane fuel through an octane enrichment reactor containing a zeolite forming catalyst and a transalkylation catalyst; and
   maintaining a $H_2$ concentration of about 20 to about 50 molar % in the octane enrichment reactor, wherein the recovery of the high octane fuel is about 50% to about 90% of the feed stream.

2. The process of claim 1, wherein the medium octane fuel is produced by
   i. passing the synthesis gas to convert synthesis gas to methanol and water, which produces a first exit through a first reactor stream;
   ii. passing the first exit stream through a second reactor to convert methanol to dimethylether, which produces a second exit stream;
   iii. passing the second exit stream through a third reactor to convert methanol and dimethylether to fuel and heavy gasoline, which produces a third exit stream;
   iv. passing the third exit stream through a fourth reactor to convert the heavy gasoline to isoparaffins, naphthenes, and less substituted aromatics, which produces a fourth exit stream;
   v. passing the fourth exit stream through a condenser to separate unreacted synthesis gas from the medium octane fuel; and
   vi. recycling the unreacted synthesis gas to the first reactor; wherein no removal or separation of the first, second or third exit streams are effected during steps a) to d).

3. The process of claim 1, wherein the medium octane fuel is produced by
   i. passing the synthesis gas through a first reactor to convert synthesis gas to methanol and water, which produces the first exit stream;
   ii. passing the first exit stream through a second reactor to convert methanol to dimethylether, which produces a second exit stream;
   iii. passing the second exit stream through a third reactor containing a third catalyst for converting methanol and dimethylether to fuel and heavy gasoline, and a fourth catalyst for converting the heavy gasoline to isoparaffins, naphthenes, and less substituted aromatics, which produces a third exit stream;
   iv. passing the third exit stream through a condenser to separate unreacted synthesis gas from the medium octane fuel; and
   v. recycling the unreacted synthesis gas, wherein no removal or separation of the first, second, or third exit streams are effected during steps a) to c).

4. The process of claim 1, wherein the zeolite forming catalyst contacts the medium octane fuel before the transalkylation catalyst.

5. The process of claim 1, wherein the zeolite forming catalyst forms a top layer in the octane enrichment reactor and the transalkylation catalyst from a bottom layer in the octane enrichment reactor.

6. The process of claim 1, where in the zeolite-forming catalyst comprises ZSM-5, ZSM-11, mordenite, chabazite, or combinations thereof.

7. The process of claim 1, wherein the transalkylation catalyst comprises Y-zeolite, beta-zeolite, or a combination thereof.

8. The process of claim 1, wherein the medium octane fuel passes through a first bed containing the zeolite forming catalyst, followed by a second bed containing the transalkylation catalyst.

9. The process of claim 1, wherein the octane enrichment reactor operates at about 350 to about 480° C. and/or about 5 bar to about 35 bar.

10. The process of claim 1, wherein the WHSV of the feed stream through the octane enrichment reactor is about 1 to about 5 $hr^{-1}$.

11. The process of claim 1, wherein the feed stream further contains $H_2$.

12. The process of claim 1, wherein the zeolite forming catalyst is doped or impregnated with a transition metal or an alkali earth metal.

\* \* \* \* \*